(12) United States Patent
Ostrovsky et al.

(10) Patent No.: US 8,287,472 B2
(45) Date of Patent: Oct. 16, 2012

(54) ULTRASOUND HEATER-AGITATOR FOR THERMAL TISSUE TREATMENT

(75) Inventors: Isaac Ostrovsky, Wellesley, MA (US); Victor Shukhat, Canton, MA (US); Jamie Li, Lexington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 260 days.

(21) Appl. No.: 12/748,964

(22) Filed: Mar. 29, 2010

(65) Prior Publication Data

US 2010/0280421 A1  Nov. 4, 2010

Related U.S. Application Data

(60) Provisional application No. 61/174,225, filed on Apr. 30, 2009.

(51) Int. Cl.
*A61H 1/00* (2006.01)
(52) U.S. Cl. .......................................................... 601/3
(58) Field of Classification Search ........................ 601/3
See application file for complete search history.

(56) References Cited

U.S. PATENT DOCUMENTS

| 4,508,122 | A | | 4/1985 | Gardineer et al. | |
|---|---|---|---|---|---|
| 5,655,537 | A | * | 8/1997 | Crowley | 600/462 |
| 5,771,896 | A | * | 6/1998 | Sliwa et al. | 600/462 |
| 7,889,346 | B2 | * | 2/2011 | Myrick et al. | 356/445 |
| 2002/0065512 | A1 | | 5/2002 | Fjield et al. | |
| 2003/0062056 | A1 | * | 4/2003 | Quan et al. | 132/148 |
| 2006/0058664 | A1 | | 3/2006 | Barthe et al. | |
| 2008/0007142 | A1 | * | 1/2008 | Toda | 310/335 |
| 2009/0014550 | A1 | * | 1/2009 | Babaev | 239/102.1 |
| 2009/0084734 | A1 | * | 4/2009 | Yencho | 210/741 |

* cited by examiner

*Primary Examiner* — Tse Chen
*Assistant Examiner* — Hien Nguyen
(74) *Attorney, Agent, or Firm* — Fay Kaplun & Marcin, LLP

(57) ABSTRACT

A method and a device to deliver heat and mechanical agitation in a liquid with ultrasound. The method and device may be used for thermal treatment of tissue within a living body, the device comprises a housing extending from a distal end to a proximal end, the housing including a first opening exposing an inner chamber of the device to the fluid, the housing being sized and shaped for insertion to a target location within the body and a piezoelectric element fixed within the housing and generating pulses of ultrasound energy directed substantially along a longitudinal axis of the housing in combination with first and second deflecting elements, the first deflecting element being mounted within the housing on a distal side of the piezoelectric element, the second deflecting element being mounted within the housing on a proximal side of the piezoelectric element, the first and second deflecting elements deflecting a portion of ultrasound energy from the piezoelectric element away from the axis of the housing so that the deflected ultrasound energy exits the housing via the first opening.

15 Claims, 5 Drawing Sheets

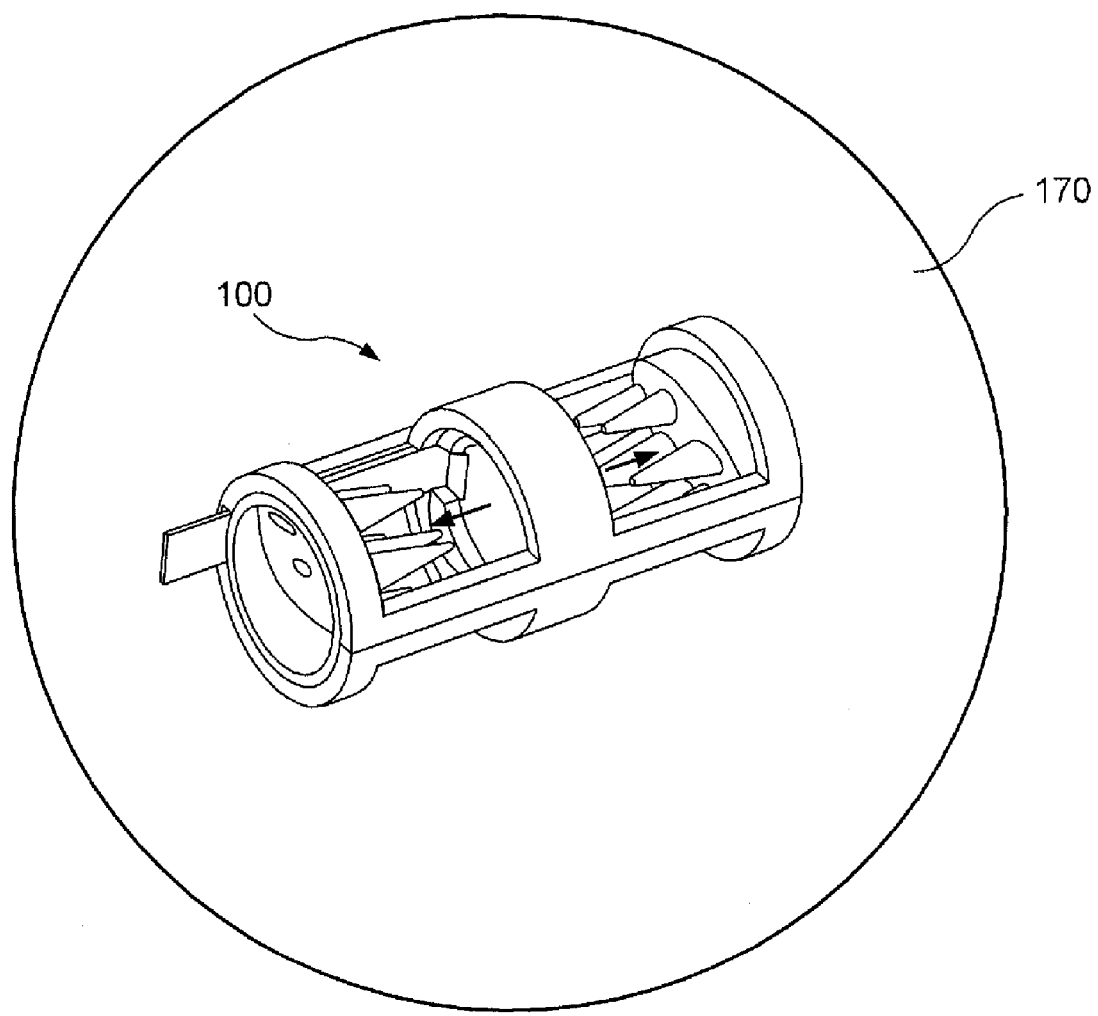
F I G. 4

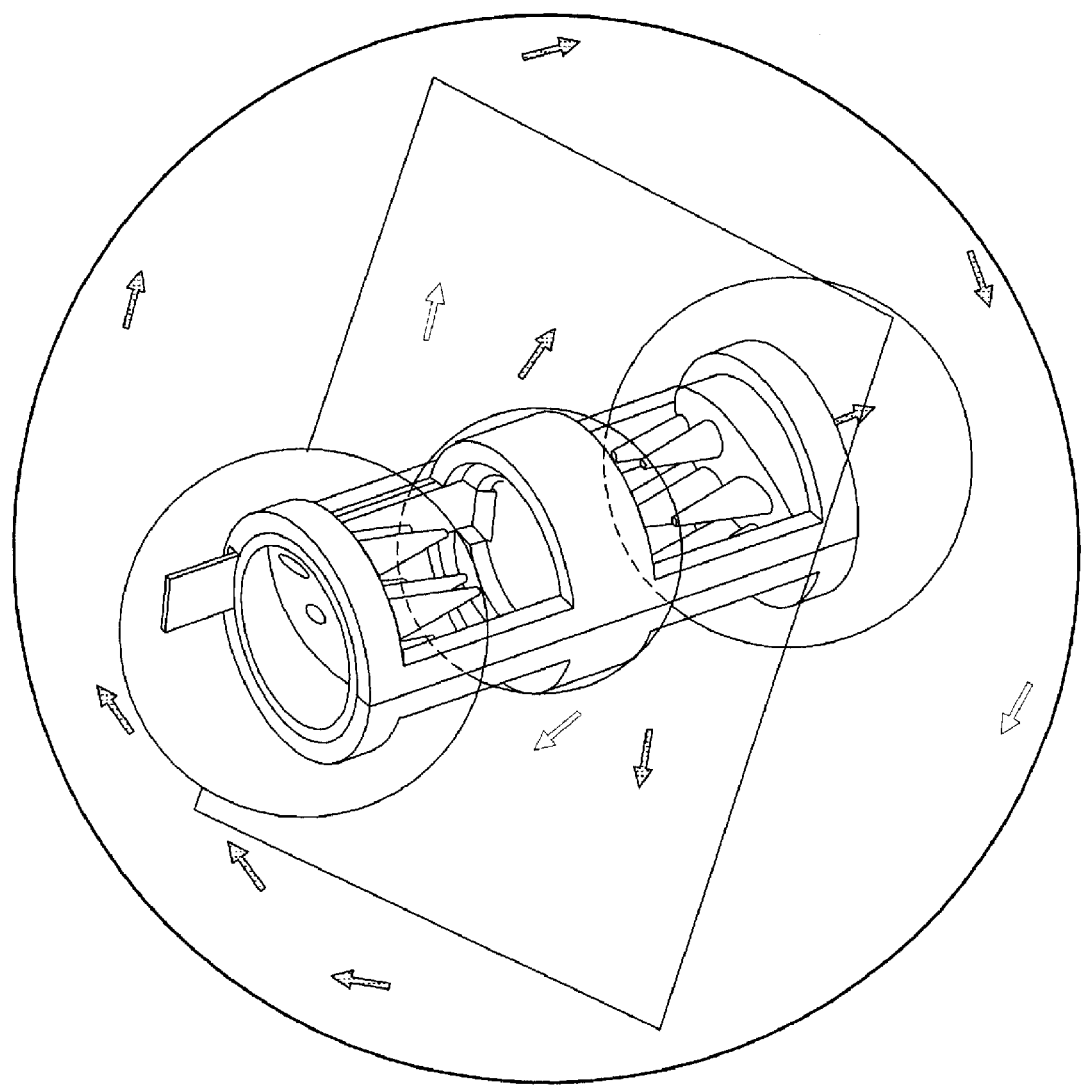
F I G. 5

ULTRASOUND HEATER-AGITATOR FOR THERMAL TISSUE TREATMENT

PRIORITY CLAIM

This application claims the priority to the U.S. Provisional Application Ser. No. 61/174,225, entitled "Ultrasound Heater-Agitator for Thermal Tissue Treatment" filed on Apr. 30, 2009. The specification of the above-identified application is incorporated herewith by reference.

BACKGROUND sound energy has been applied to tissue for various thermal treatments and has been used in mechanical actuators based on motion/deformation of a piezoelectric element. Separately, heated fluids have been employed in the thermal treatment of tissue such as ablation. For example, in hydrothermal ablation, fluid heated to approximately to 90° C. is introduced into the uterus to ablate the lining thereof. To ensure even temperature distribution, this fluid must be agitated and circulated within the uterus via, for example, an external heater and pump. The fluid is heated as it passes through the heater while being pumped in a cycle into and out of the uterus. However, as this fluid circulates in and out of an organ such as the uterus, tissue particles in the fluid may become lodged in the external heater or the pump reducing the circulation of the fluid and the uniformity of the ablation of the endometrium.

SUMMARY OF THE INVENTION

The present invention is a method and a device to deliver heat and mechanical agitation to a liquid. More specifically, the present invention is directed to a method and device for thermal treatment of tissue within a living body, the device comprises a housing extending from a distal end to a proximal end, the housing including a first opening exposing an inner chamber of the device to the fluid, the housing being sized and shaped for insertion to a target location within the body and a piezoelectric element fixed within the housing and generating pulses of ultrasound energy directed substantially along a longitudinal axis of the housing in combination with first and second deflecting elements, the first deflecting element being mounted within the housing on a distal side of the piezoelectric element, the second deflecting element being mounted within the housing on a proximal side of the piezoelectric element, the first and second deflecting elements deflecting a portion of ultrasound energy from the piezoelectric element away from the axis of the housing so that the deflected ultrasound energy exits the housing via the first opening. In general, this invention reveals a method and device to deliver heat and agitation in a liquid using ultrasound.

The present invention is further directed to a method, comprising immersing a device in a fluid within a living body, the device including a housing extending from a distal end to a proximal end and including openings exposing an inner chamber of the device to the fluid, a piezoelectric element mounted within the housing aligned so that, when excited, the piezoelectric element generates pulses of ultrasound energy directed substantially along a longitudinal axis of the housing and first and second deflecting elements, the first deflecting element being mounted within the housing on a distal side of the piezoelectric element and the second deflecting element being mounted within the housing on a proximal side of the piezoelectric element. The piezoelectric element is excited to generate ultrasound energy of a desired frequency and amplitude directed toward the first and second deflecting elements so that a portion of the ultrasound energy impinging on the first and second deflecting elements is deflected therefrom to target tissue.

BRIEF DESCRIPTION OF THE DRAWINGS

FIG. 4 shows the device of FIG. 1 in which a piezoelectric element generates ultrasound energy; and FIG. 5 shows the device of FIG. 1 heating and agitating a fluid.

DETAILED DESCRIPTION

The present invention, which may be further understood with reference to the following description and the appended drawings, relates to devices for thermal treatment of tissue. Exemplary embodiments of the present invention heat and/or agitate fluids within a living body (e.g., within a hollow organ) to treat tissue. One exemplary procedure that will be described below is hydrothermal ablation of the lining of the uterus. It should be noted, however, that although the embodiments of the present invention are described in regard to the ablation of the endometrium, the invention is relevant to the use of an ultrasound device which heats fluids within the body for any thermal treatment of tissue and may be employed, for example, in organs such as the urinary bladder, the stomach, etc.

Figure 1:
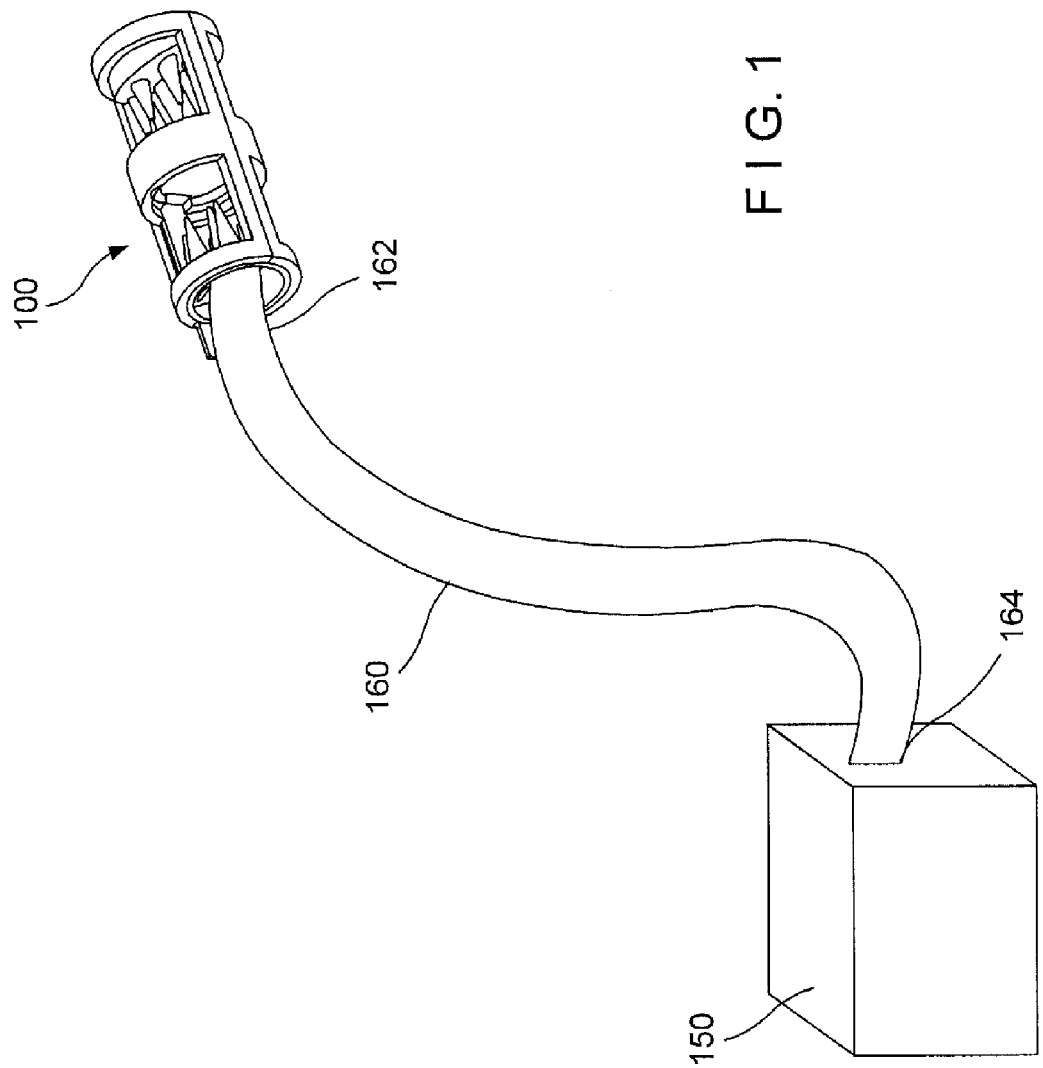
FIG. 1 shows a perspective view of a device according to an exemplary embodiment of the present invention.
Figure 2:
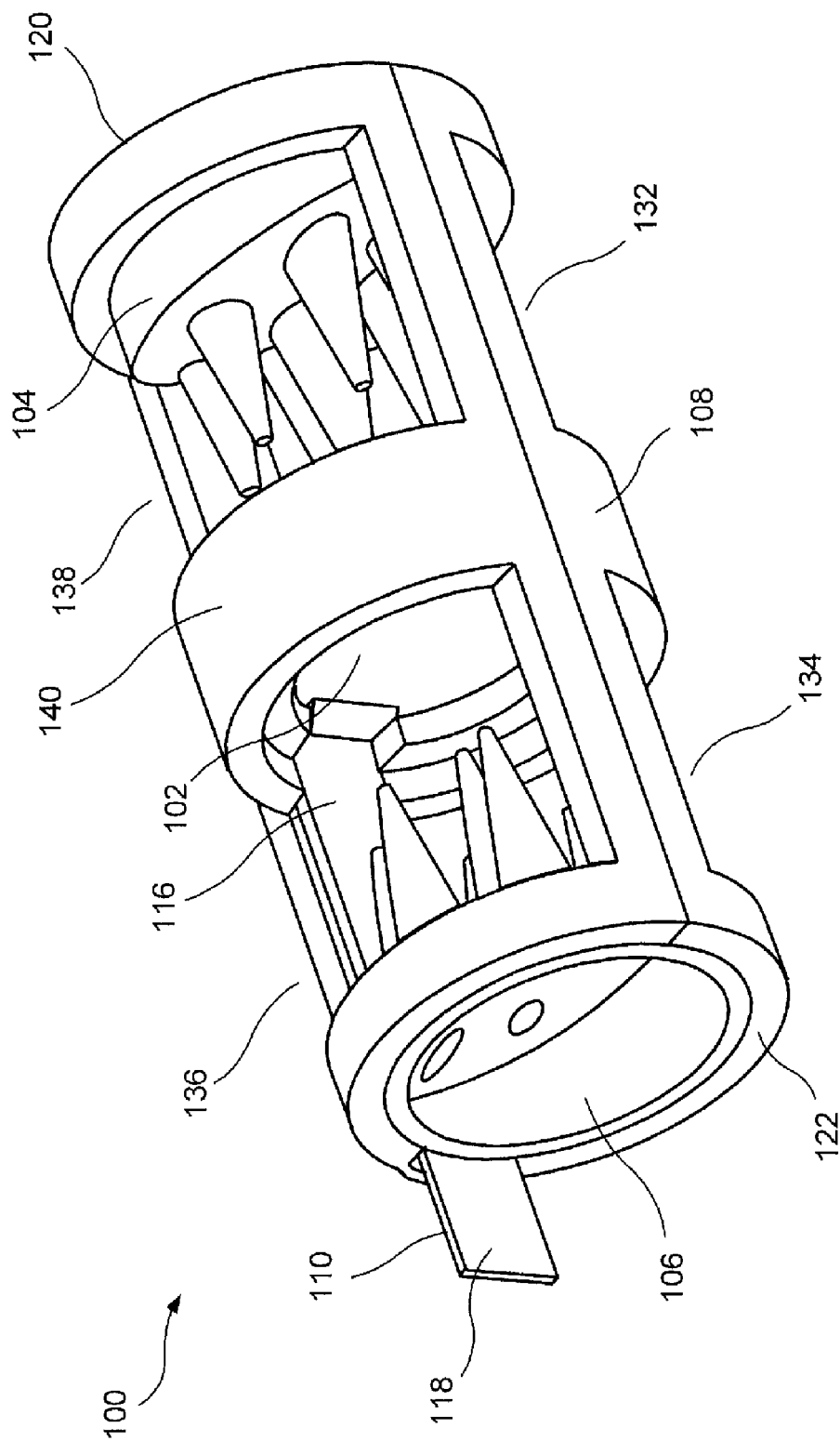
FIG. 2 shows an enlarged perspective view of the device of FIG. 1.

FIGS. 1-5 show a device 100 according to an exemplary embodiment of the present invention. As shown in FIG. 1, the device 100 may be connected to an external power source 150 via a flexible elongate member 160. The device 100 may be mounted on a distal end 162 of the elongate member 160 while the power source 150 may be connected to a proximal end 164 such that the power source 150 may remain external to the body when the device 100 is inserted into the body. Once inserted, the device 100 may be immersed in a fluid 170 within the body (e.g., within an organ such as the uterus). As shown in FIG. 2, the device 100 may further comprise a piezoelectric element 102, a pair of deflecting elements 104, 106, a housing 108 and a transmission line 110. The piezoelectric element 102 and the deflecting elements 104, 106 between which the piezoelectric element 102 is positioned are held in the housing 108 while the transmission line 110 extends from the piezoelectric element 102 to the external power source 140 along or within the elongate member 160 to transmit power (e.g., RF energy) from the power source 150 to the device 100.

Figure 3:
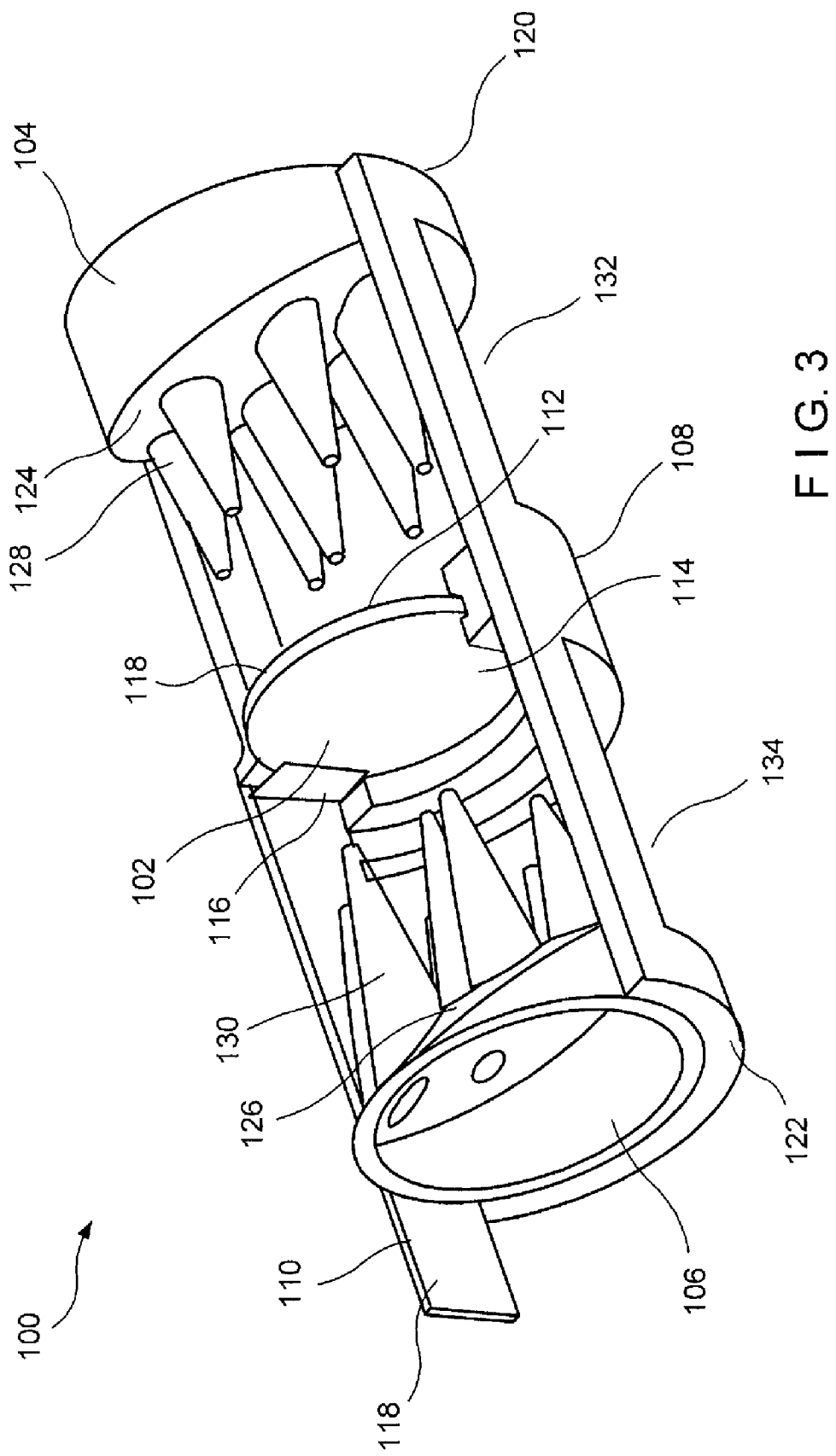
FIG. 3 shows an enlarged perspective view of the device of FIG. 1 with a portion of a housing of the device removed.

As shown in FIG. 3, the piezoelectric element 102 may be formed as a thin, substantially flat disc fixed within the housing 108 with first and second surfaces 112, 114, respectively, thereof substantially exposed while an outer perimeter 116 thereof remains encased by the housing 108. The piezoelectric element 102 may be manufactured of any known material exhibiting a piezoelectric effect such as, for example, crystals and ceramics. One such suitable material is PZT (i.e., lead zirconate titanate). As understood by those skilled in the art, the piezoelectric effect generates mechanical stress in the material when an electric potential is applied thereto. Thus, the first and second surfaces 112, 114 are metal-plated (e.g., silver, nickel and gold) such that an electric potential may be applied across the piezoelectric element 102. The transmission line 110 may be formed, for example, as an elongated electrically conducting member a distal end 116 of which is attached to the piezoelectric element 102 while a proximal end 118 thereof is accessible at a proximal end 122 of the device 100 for coupling to an external source of electric energy 150. When pulsed electrical energy is transferred to the piezoelectric element 102 via the transmission line 110, the changes in electric potential applied thereto cause the piezoelectric element 102 to vibrate, creating pressure pulses adjacent to the first and second surfaces 112, 114. Ultrasound energy in the form of pulses in the fluid 170 moves away from the first and second surfaces 112, 114, substantially perpendicular to those surfaces as shown in FIG. 3. As the piezoelectric element 102 is positioned between the two deflecting elements 104, 106, the ultrasound energy is reflected out of the housing 108 from one of the deflecting elements 104, 106.

The deflecting elements 104, 106 are fixed to the housing 108 on either side of the piezoelectric element 102 with the distal surface 112 of the piezoelectric element 102 facing a first one of the deflecting elements 104 while the proximal surface 114 faces the second deflecting element 106. The first deflecting element 104 is fixed at a distal end 120 of the housing 108 while the second deflecting element 106 is fixed at the proximal end 122 of the housing 108. The arrangement of the piezoelectric element 102 within the housing 108 generating pulses directed substantially along the longitudinal axis thereof and deflecting elements 104, 106 to diffuse and redirect this ultrasound energy out of the housing 108 prevents the bulk of the ultrasound energy from directly impacting and burning the tissues of the uterus. The deflecting elements 104, 106 are preferably shaped such that the ultrasound energy from the piezoelectric element 102 is not directly reflected therefrom but is scattered to distribute the energy over a wider tissue surface area. For example, a surface 124 of the deflecting element 104 and a surface 126 of the deflecting element 106 may be substantially spherically convex such that the pulses of ultrasound energy are dispersed upon reflection therefrom. Each of the surfaces 124, 126 may also include a plurality of protrusions 128, 130, respectively, which roughen the surfaces 124, 126 to further scatter the ultrasound energy in various directions. To deflect the ultrasound energy in a directional stream for better heat transfer and distribution to a desired target area, the surfaces 124, 126 may be angled with respect to a plane of the piezoelectric element 102. In a preferred embodiment, the surface 124 may be angled in a direction opposite that of the surface 126 such that pulses of ultrasound energy which contact these angled surfaces 124, 126 are scattered in opposite directions to form a generally circulatory pattern of fluid flow. Thus, the surface 124 agitates the fluid 170, causing it to circulate through the organ without being overwhelmingly directed to a single spot which would otherwise be burned.

If desired, the deflecting elements 104, 106 may be formed to absorb a portion of the ultrasound energy and convert it to heat to heat the surrounding fluid 170. The deflecting elements 104, 106 may be formed of a thermally conductive ceramic, such as Aluminum Silicone Carbide, which is manufactured by CPS Technologies Corporation (Norton, Mass.). A thermally conductive material allows for quick heat dissipation. For optimal coupling of the ultrasound energy, an acoustic impedance of the ceramic should match the acoustic impedance of the fluid 170. It will be understood by those of skill in the art that the closer the two values are to one another, the more acoustic energy the deflecting elements 104 will absorb. For example, the acoustic impedance of ceramic, $Z_{ceramics}$=~36 Mrayls, while the acoustic impedance of a fluid 170 such as water is $Z_{water}$=1.5 Mrayls. Because of the substantial difference in acoustic impedance values, the deflecting element 104 will have difficulty coupling the ultrasound energy. However, any ultrasound energy that is coupled from the fluid into the deflectors, would be quickly converted into heat which would then be conducted into the fluid. A significant portion of the ultrasound energy impinging on the deflecting elements 104, 106 will be reflected from the deflecting elements 104, 106 because of the difference in acoustic impedance between the water and the material of the deflecting elements 104, 106. Thus, a desired ratio of ultrasound energy reflected from the deflecting elements 104, 106 to energy coupled and absorbed thereby, may be achieved by selecting a composition of the deflecting elements 104, 106 to have an acoustic impedance which differs from that of the fluid 170 by an amount corresponding to the desired ratio.

So that the deflecting elements 104, 106 may better couple the ultrasound energy, the surfaces 124, 126 thereof may be coated with a thin layer of thermally conductive UV cured epoxy, filled with ceramic powder. One example of such an epoxy is manufactured by Dymax Corportation (Torrington, Conn.). The acoustic impedance of this UV cured epoxy layer is $Z_{layer}$=~5-7 Mrayls, which would make the acoustic impedance of the deflecting elements 104, 106 very close in value to the acoustic impedance of water since the acoustic impedance of the perfect matching layer would be calculated as $Z_{layer}=\sqrt{(Z_{water} \times Z_{ceramics})}=\sqrt{(1.5 \times 36)}=7.3$ Mrayls. For this particular Dymax manufactured UV cured epoxy layer, the thickness of the layer may be a multiple of an odd number of quarter wavelengths (i.e., $(2n+1) \times \frac{1}{4}\lambda$). The wavelength, $\lambda$ is a function of a sound velocity in the material V and frequency F of the piezoelectric element vibration with $\lambda=V/F$. For example, if the velocity of sound in the ceramic filled epoxy is $V=2\times10^6$ mm/sec and the frequency of excitation of the piezoelectric element is $F=16$ MHz=$16\times10^6$ cycles/sec, then $\lambda=(2\times10^6$ mm/sec$)/(16\times10^6$ cycles/sec$)=0.125$ mm. This wavelength may be used to determine a desired thickness of the matching layer. It will be understood by those of skill in the art that various matching layers and frequencies may be used depending on the fluid 170 within which the piezoelectric element 102 will be immersed and on the material of the piezoelectric element 102. It will also be understood by those of skill in the art that higher the frequencies allows for faster absorption of the ultrasound energy by the fluid 170 and the deflecting elements 104, 106. In a preferred embodiment, the frequency may range from 5-100 MHz.

In another embodiment, the deflecting elements 104, 106 may be formed of a highly porous hydrophilic ceramic. An example of such a material is manufactured by Soilmoisture Equipment Corporation (Santa Barbara, Calif.). The open pore structure of the material provides a convoluted path of interconnecting networking channels, allowing a complete flow throughout the material for migrating fluid 170. This allows efficient coupling of the mechanical energy from the fluid 170 into the deflecting elements 104, 106 and conversion of the energy into heat within the deflecting elements 104, 106. It will be understood by those of skill in the art that a variety of porous materials may be selected for the deflecting elements 104, 106 depending on an appropriate pore size and void volume, which would be selected for optimal performance.

As would be understood by those skilled in the art, the device 100 may include a flexible insertion section similar to those of endoscopes and other minimally invasive surgical instruments with the housing 108 mounted at a distal end thereof. For such a device 100, the housing 108 which encases the piezoelectric element 102 and the deflecting elements 104, 106 will be sized and shaped such that the device 100 may be inserted into the body via a naturally occurring bodily orifice and advanced through a body lumen to a target site therein or to an extralumenal target site. The housing 108 may be a substantially longitudinal and hollow member extending from the distal end 120 to the proximal end 122. The distal and proximal ends 120, 122 may be open such that the deflecting elements 104, 106, fixed within the housing 108 at these ends 120, 122 are exposed. The housing 108 may also include cut-outs 132, 134, 136, 138 through a surface 140 of the housing 108 to facilitate the transfer of energy from the piezoelectric element 102 to the surrounding area. The cut-outs 132, 134, 136, 138 may cover a substantial surface area of the housing 108 such that the first and second surfaces 112, 114 and the surfaces 124, 126 of the deflecting elements 104, 106 are substantially exposed to the outside of the device 100. The cut-outs 132, 134, 136, 138 allow ultrasound energy in the form of pulses of fluid to easily pass through the device 100 such that the surrounding fluid 170 may be heated and agitated thereby. It will be understood by those of skill in the art that although the device 100 is shown in FIGS. 1-5 as including four cut-outs, the housing 108 may include any number of cut-outs so long as an interior of the housing 108 is exposed to the exterior of the device 100 such that ultrasound energy may easily pass therethrough.

The fluid 170 may be water, as described above, saline, or another other fluid appropriate for hydrothermal ablation or any other thermal treatment utilizing heated fluid 170. The fluid 170 may be supplied to the uterus, or any other treatment site via a catheter or other fluid supply tool as would be understood by those skilled in the art. After the fluid 170 has been supplied to the treatment site, the device 100 may be inserted into the organ via a naturally occurring orifice in the body or via any other opening (e.g., a surgical incision). Once at the treatment site, the device 100 is immersed in the fluid 170 and RF energy is delivered to the piezoelectric element 102. As described above, the RF energy excites and vibrates the piezoelectric element 102 generating ultrasound energy in the form of pulses of fluid pressure moving away from the first and second surfaces 112, 114 toward the deflecting elements 104, 106 as shown in FIG. 4. This ultrasound energy is depicted by the directional arrows in FIG. 4. The pulses of energy move substantially perpendicularly to the piezoelectric element 102, to impinge on the surfaces 124, 126 of the deflecting elements 104, 106 which face the piezoelectric element 102.

Some of the beams of energy that hit the piezoelectric element 102 will be absorbed by the deflecting elements 104, 106 while some of the energy will be deflected by the angled surfaces 124, 126 of the deflecting elements 104 setting up a substantially circular fluid motion, as depicted in FIG. 5. The angles of the surfaces 124, 126 ensure that fluid pulses leaving the surfaces 124, 126 exit the housing 108 via the cutout 132, 134, 136, 138 shown in FIG. 2. In a preferred embodiment, the surfaces 124, 126 are positioned at opposite angles relative to one another such energy is deflected from these surfaces in opposite directions—i.e., diametrically opposed relative to a longitudinal axis of the housing 108. For example, energy leaving the first surface 112 of the piezoelectric element 102 deflected from the surface 124 of the deflecting element 104 exits the housing 108 via the cut-out 132. A portion of the energy deflecting off tissue (e.g., a wall of a body cavity within which the device 100 is located) may re-enter the housing 108 via cut-out 134. Likewise, energy leaving the second surface 114 of the piezoelectric element 102 deflected from the surface 126 of the deflecting element 106 exits the housing 108 via the cut-out 136. A portion of the energy deflecting off of the tissue may re-enter the housing 108 via cut-out 138. Thus, the beams of energy are able to create a substantially circular pattern of motion.

Additionally, the spherically convex shape of the surfaces 124, 126, along with the protrusions 128, 130, scatter the ultrasound beams. The scattering also aids to de-focus the ultrasound beams such that the beams lacks the intensity necessary to produce a burn when it enters the tissue. An amount of energy that is absorbed by the deflecting elements 104, 106 will be dependent upon the acoustic impedance of both the fluid and the deflecting elements 104, 106. The energy and fluid 170 that is absorbed by the deflecting elements 104, 106 are converted to heat such that the surrounding fluid 170, or the fluid 170 within the deflecting elements 104, 106 if the material is highly porous, may be heated. As the deflecting elements 104, 106 also keeps the fluid 170 moving circularly through the organ, the heated fluid 170 is agitated and distributed evenly through the organ.

It will be apparent to those skilled in the art that various modifications and variations can be made in the structure and the methodology of the present invention, without departing from the spirit or scope of the invention. Thus, it is intended that the present invention cover modifications and variations of the invention provided that they come within the scope of the appended claims and their equivalents.

What is claimed is:

1. A device for thermal treatment of tissue within a living body, device comprising:
   a housing extending from a distal end to a proximal end, the housing including a first opening exposing an inner chamber of the device to the fluid, the housing being sized and shaped for insertion to a target location within the body;
   a piezoelectric element fixed within the housing and generating pulses of ultrasound energy directed substantially along a longitudinal axis of the housing; and
   first and second deflecting elements, the first deflecting element being mounted within the housing on a distal side of the piezoelectric element, the second deflecting element being mounted within the housing on a proximal side of the piezoelectric element, the first and second deflecting elements deflecting a portion of ultrasound energy from the piezoelectric element away from the axis of the housing so that the deflected ultrasound energy exits the housing via the first opening, one of the first and second deflecting elements including a plurality of protrusions scattering a portion of the energy deflected thereby and wherein one of the first and second deflecting elements is formed of a porous material with an interconnecting network of channels so that fluid flows through the one of the first and second deflecting elements that is formed of a porous material.

2. The device of claim 1, further comprising:
   a transmission line connecting the piezoelectric element to a power source which remains outside the body during use.

3. The device of claim 1, wherein the first and second deflecting elements are tilted relative to the longitudinal axis of the housing.

4. The device of claim 3, wherein the housing further includes a second opening, the first and second openings being located on sides of the housing opposite one another with respect to the longitudinal axis.

5. The device of claim 4, wherein the first deflecting element is angled to deflect ultrasound energy out of the first opening and the second deflecting element is angled to deflect ultrasound energy out of the second opening.

6. The device of claim 1, wherein a surface of one of the first and second deflecting elements is convex such that ultrasound energy deflected therefrom is diffused.

7. The device of claim 1, wherein one of the first and second deflecting elements is formed of a thermally conductive ceramic to absorb a portion of the ultrasound energy impinging thereon.

8. The device of claim 1, wherein a surface of one of the first and second deflecting elements is coated with a thermally conductive UV cured epoxy.

9. The device of claim 1, wherein the piezoelectric element is formed of one of a crystal and a ceramic.

10. The device of claim 1, wherein the piezoelectric element includes a metal coating.

11. A method, comprising:
   immersing a device in a fluid within a living body, the device including:
   a housing extending from a distal end to a proximal end and including openings exposing an inner chamber of the device to the fluid;
   a piezoelectric element mounted within the housing aligned so that, when excited, the piezoelectric element generates pulses of ultrasound energy directed substantially along a longitudinal axis of the housing; and
   first and second deflecting elements, the first deflecting element being mounted within the housing on a distal side of the piezoelectric element and the second deflecting element being mounted within the housing on a proximal side of the piezoelectric element, wherein one of the first and second deflecting elements includes a plurality of protrusions scattering ultrasound energy impinging there against; further one of the first and second deflecting elements is formed of a porous material with an interconnecting network of channels so that fluid flows through the one of the first and second deflecting elements that is formed of a porous material; and
   exciting the piezoelectric element to generate ultrasound energy of a desired frequency and amplitude directed toward the first and second deflecting elements so that a portion of the ultrasound energy impinging on the first and second deflecting elements is deflected therefrom to target tissue.

12. The method of claim 11, wherein the first and second deflecting elements are oriented to direct ultrasound energy deflected therefrom out of opposite sides of the housing to generate a substantially circular flow.

13. The method of claim 11, wherein one of the first and second deflecting elements is constructed to scatter a portion of the ultrasound energy deflected therefrom to distribute the ultrasound energy over a wider tissue surface area.

14. The method of claim 11, further comprising:
   inserting the device into a hollow organ via a body lumen.

15. The method of claim 14, wherein the body lumen is accessed via a naturally occurring bodily orifice.

* * * * *